United States Patent
Henry et al.

(10) Patent No.: US 7,113,826 B2
(45) Date of Patent: Sep. 26, 2006

(54) ATRIAL ARRHYTHMIA DETECTION FOR AN ACTIVE IMPLANTABLE MEDICAL DEVICE

(75) Inventors: Christine Henry, Paris (FR); Marcel Limousin, Paris (FR)

(73) Assignee: ELA Medical S.A.S., Montrouge (FR)

( * ) Notice: Subject to any disclaimer, the term of this patent is extended or adjusted under 35 U.S.C. 154(b) by 547 days.

(21) Appl. No.: 10/283,376

(22) Filed: Oct. 29, 2002

(65) Prior Publication Data
US 2003/0097156 A1 May 22, 2003

(30) Foreign Application Priority Data
Oct. 30, 2001 (FR) ................................ 01 13990

(51) Int. Cl.
*A61N 1/37* (2006.01)
(52) U.S. Cl. .......................... 607/28; 607/14; 607/27; 600/510
(58) Field of Classification Search .................. 607/9, 607/14, 27–28; 600/509–510
See application file for complete search history.

(56) References Cited

U.S. PATENT DOCUMENTS

| | | | |
|---|---|---|---|
| 5,658,320 A | 8/1997 | Betzold et al. | ............... 607/14 |
| 6,169,918 B1* | 1/2001 | Haefner et al. | ............. 600/509 |
| 6,249,701 B1* | 6/2001 | Rajasekhar et al. | ............. 607/9 |
| 6,738,665 B1* | 5/2004 | Poezevara et al. | ............. 607/9 |
| 2002/0147472 A1* | 10/2002 | Seim et al. | ................... 607/14 |

FOREIGN PATENT DOCUMENTS

| | | |
|---|---|---|
| EP | 1 072 284 A2 | 1/2001 |
| EP | 1 123 716 A2 | 8/2001 |
| WO | WO 00/24460 | 5/2000 |
| WO | WO 00/47277 | 8/2000 |

* cited by examiner

*Primary Examiner*—Robert E. Pezzuto
*Assistant Examiner*—Tammie K. Heller
(74) *Attorney, Agent, or Firm*—Orrick Herrington & Sutcliffe, LLP

(57) ABSTRACT

Apparatus for detecting atrial arrhythmias in the treatment of disorders of the heartbeat rate in active implantable medical devices of the pacemaker, cardioverter, defribillator and/or multisite type. This device includes conventional systems, circuits and control algorithm for detecting spontaneous and stimulated ventricular events (R, V) and atrial events (P, A), indicating the delivery of a ventricular and/or atrial event, and inhibiting the detection of atrial events after detection of a ventricular event throughout a post-ventricular atrial absolute refractory period (PVAARP). Detecting atrial events includes protecting against the detection of atrial signals that do not correspond to an atrial event that has actually occurred, in particular protecting against atrial detection of far-field signals caused by a ventricular event. The protection operates by a dynamic adjustment of the sensitivity of detection by temporarily raising ($t_1$, $t_2$) a detection threshold ($\Delta S_1$, $\Delta S_2$) after detection of a ventricular event without detection of a preceding (spontaneous or stimulated) atrial event during the same cardiac cycle.

18 Claims, 2 Drawing Sheets

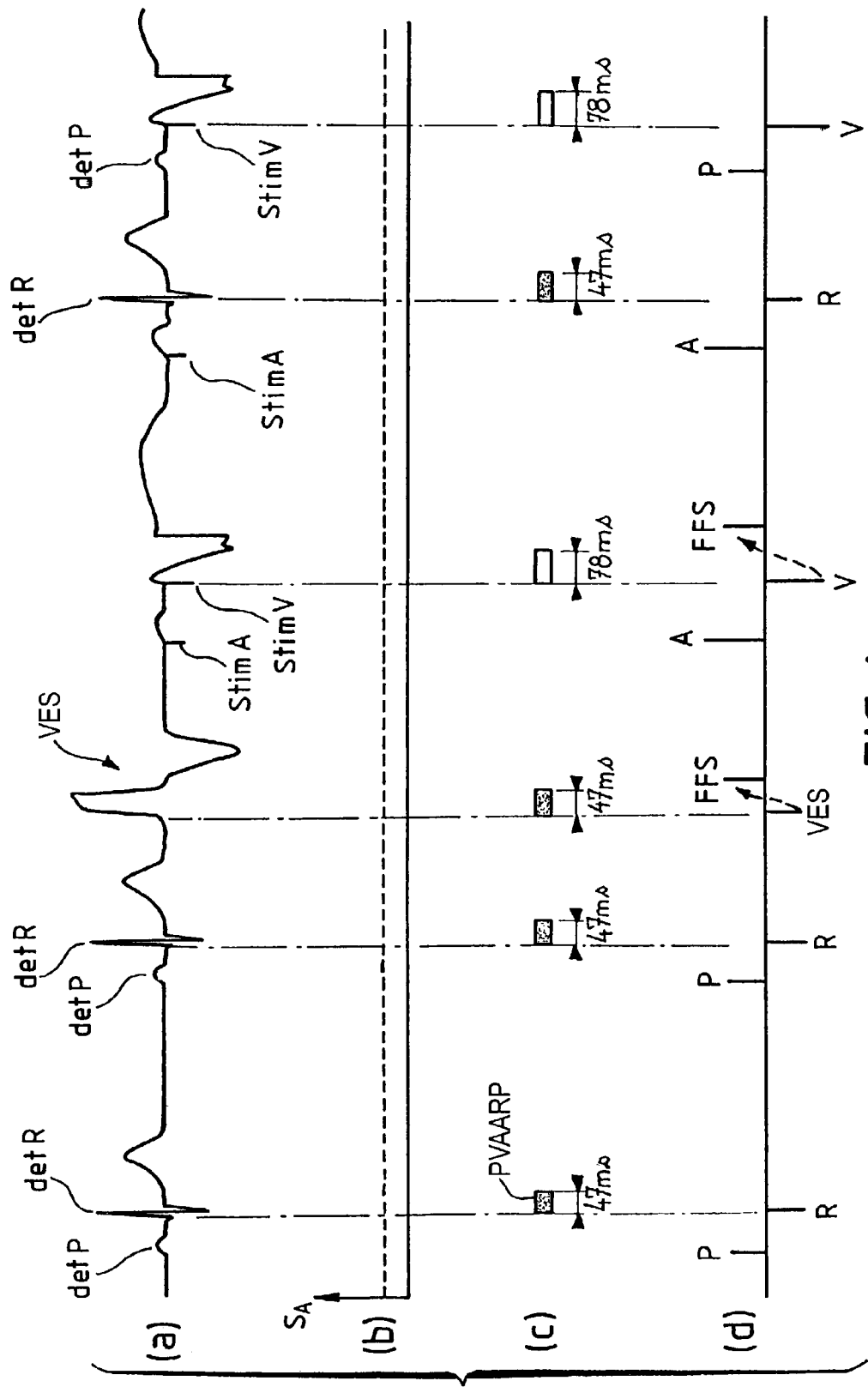
FIG_1

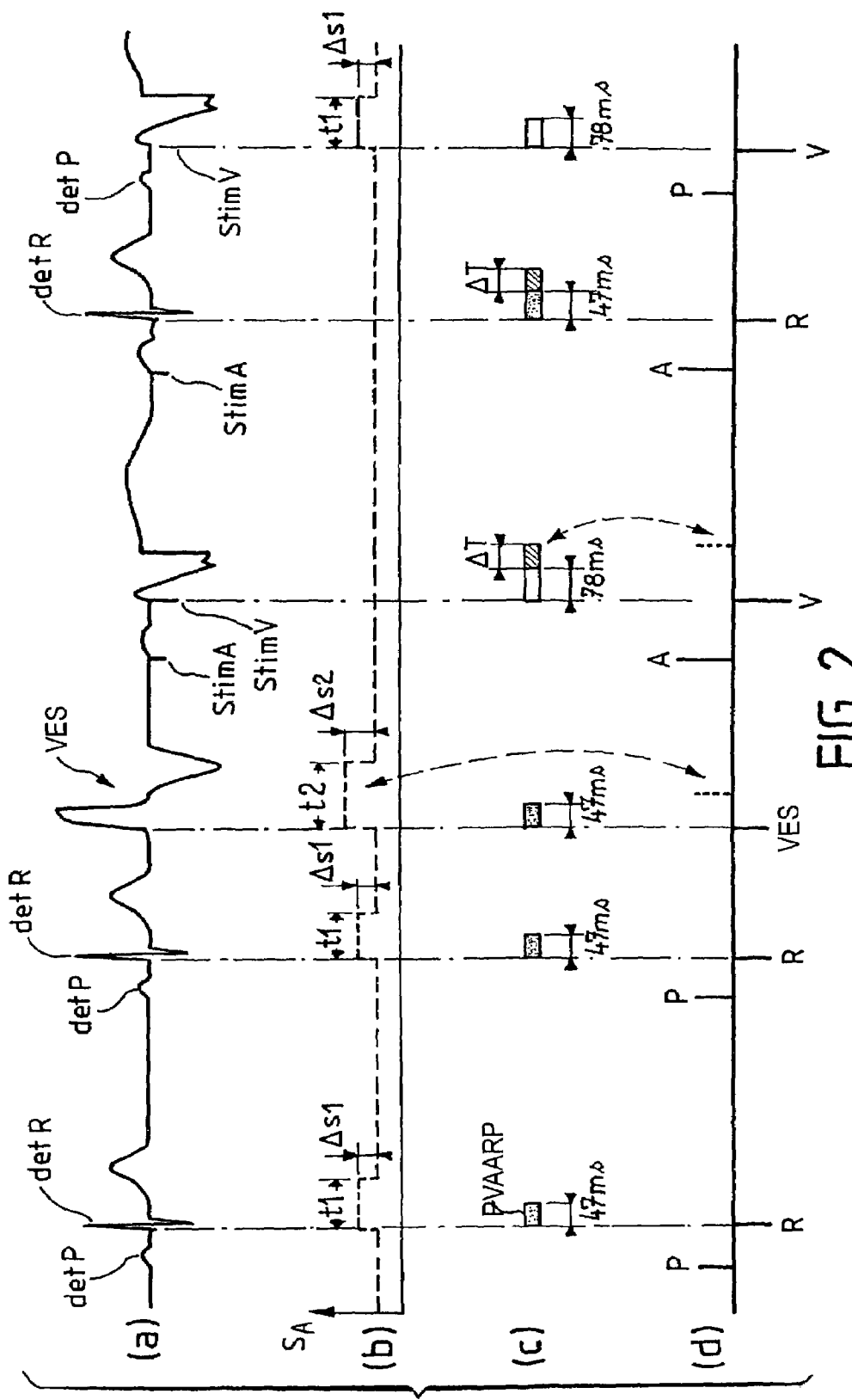

ATRIAL ARRHYTHMIA DETECTION FOR AN ACTIVE IMPLANTABLE MEDICAL DEVICE

FIELD OF THE INVENTION

The present invention relates to "active implantable medical devices" as such devices are defined by the Jun. 20, 1990 directive 90/385/CEE of the Council of the European Communities, more particularly to devices such as cardiac pacemakers, defibrillators, cardiovertors, and/or "multisite devices" that are able to deliver to the heart low energy stimulation pulses for the treatment of disorders of the heartbeat rate. Although the invention will be mainly described in the context of an implantable apparatus intended to treat tachycardias and tachyarrhythmias, such as a cardiovertor or a defibrillator, it should be understood that it also can be applied to apparatus intended to treat bradycardia, such as cardiac pacemakers, and, indeed, it is possible that these two categories of devices can be combined into a single apparatus employing the present invention.

BACKGROUND OF THE INVENTION

Sensing of the signals resulting from atrial cardiac events is well known. Any of a number of detection systems that include the conventional discrete circuits for signal acquisition, conditioning and typically conversion to digital values followed by digital signal processing for detecting electrical activity in the heart, including the atrium, can be used. These detection systems are also typically referred to as detection circuits. In particular, the sensitivity of a detection circuit for detecting the signals resulting from the atrial cavity is programmed to a sensitivity value that is considered high, i.e., a threshold for the detection of atrial events that is relatively low (typically about 0.4 mV). This high sensitivity (low detection threshold) is required to be able to sense and to interpret low amplitude signals in the atrium in the case of disorders of the atrial rate. The term "disorders of the atrial rate" is a generic term that covers a variety of atrial arrhythmias such as atrial tachycardia, atrial fibrillation, atrial flutter, etc.; disturbances that are characterized, during the detection, by an abnormal and fast atrial rate. In conventional cardiac detection circuits, the atrial sensitivity is a programmable parameter, but is generally fixed at a constant value, at least during the same cardiac cycle.

The high sensitivity necessarily results in false detections (known as false positives), i.e., a detection in the atrial cavity of signals not corresponding to a spontaneous atrial event (that is, a spontaneous depolarization of the myocardium in the atrium, also called a "detected atrial event") or a stimulated atrial event (that is, a depolarization caused by an application of a stimulation pulse on the atrium, also called a "paced atrial event"). Typically, these false positive detections (also known as parasitic detections) result from a phenomenon known by the name of "far-field" or "far-field sensing" ("FFS"), that occurs when the pacemaker detects in the atrial cavity a signal resulting from a prior ventricular depolarization. In other words, the depolarization of the ventricle is propagated to the atrium and, although that signal is attenuated, its amplitude remains greater than the detection threshold and thus, comes to delude the atrial detection circuit.

A disadvantage of such an FFS detection is that it can be interpreted by the device as an atrial extrasystole. If this phenomenon is repetitive, the apparatus may interpret it as an atrial tachycardia and consequently improperly start algorithms to prevent or treat the supposed (but non-existent) atrial tachycardia. In other words, the false positive detection(s) can lead to a false diagnosis of "association" when the device detects—wrongly—atrial events (as a consequence of the far-field) as often as ventricular events (at the origin of the far-field). This phenomenon strongly penalizes the detection of a "dissociation" of the cardiac rate (i.e., when the atrial events are desynchronized and fewer in number than the ventricular events) and, in a general way, the detection of the arrhythmias of all kinds.

Devices able to provide such a modification of the sensitivity of the atrial detection circuit after an atrial event are known, such as the DEFENDERr™ or ALTO™ implantable devices marketed by Ela Médical, Montrouge France or as described in the publication WO-A-00/47277 and its corresponding U.S. Pat. 6,249,701. However, these devices operate in an undifferentiated manner that does not make it possible to eliminate the phenomenon of far-field detection nor to take into account the consequences that a ventricular extrasystole can have on the operation of these devices.

OBJECTS AND SUMMARY OF THE INVENTION

Thus, it is an object of the present invention to propose an implantable device that is able to avoid detection in the atrial chamber of a signal generated by a ventricular depolarization (i.e., a far-field detection).

Another object of the present invention is to avoid detecting such a far-field signal at the time of a ventricular tachycardia, often characterized by a succession of ventricular events not preceded by a true atrial signal (i.e., a dissociated cardiac rate). More particularly, if a patient presents ventricular events that are not preceded by a P-wave (as in the case of a ventricular extrasystole ("VES")), the detection of such events at the atrium is prejudicial to the correct operation of the implant.

To this end, the present invention proposes an active implantable medical device including circuits to detect ventricular and atrial events, means for indicating delivery of a stimulation pulse to a ventricle and/or an atrium, and means for inhibiting the detection of an atrial event after detection of a ventricular event during the length of a post-ventricular, atrial, absolute refractory period ("PVAARP"), the detecting means of atrial event detection circuit comprising means for protecting against detection of an atrial signal not corresponding to an actual atrial event, more preferably protecting against detection of a ventricular event far-field signal.

In a manner characteristic of the invention, the detection circuit protecting means preferably comprises means for dynamically adjusting the sensitivity of the atrial event detection circuit by a first amount for a first length of time to inhibit detecting signals at the atrium in certain conditions.

More preferably, the dynamic adjustment is made by temporarily raising the detection threshold by a first increment for a first length of time, after detection by the ventricular detecting means of a ventricular event without detection of a prior spontaneous or stimulated atrial event, during the same cardiac cycle.

Advantageously, the dynamic adjustment of the sensitivity in accordance with a preferred embodiment of the present invention also is able to temporarily raise the detection threshold by a second increment for a second length of time, after detection of a ventricular event and a preceding spontaneous atrial event during the same cycle. The first and second increments can be of the same value, for example, a value selected from between 0.2 and 0.6 mV, preferably approximately 0.4 mV. The first and second durations can be of the same value, for example, a value selected from between 150 and 200 ms, preferably approximately 172 ms. Of course, the increments and/or duration values need not be identical or limited to the aforementioned values.

According to a second aspect of the invention, the protecting means comprises means for increasing the aforementioned post-ventricular, atrial absolute refractory period either by one predetermined duration or to a predetermined duration, after detection of a ventricular event and a preceding stimulated atrial event during the same cardiac cycle. The post-ventricular, atrial absolute refractory period can, for example, be increased by a duration that is selected from between 85 and 105 ms, preferably approximately 94 ms.

One implementation of the present invention is directed to apparatus for detecting cardiac activity in an active implantable medical device comprising a system for monitoring electrical activity in an atrium and a ventricle of a patient, the system including a circuit to receive electrical signals respectively from the atrium and from the ventricle, optionally to condition the received signals, and to convert the received signals to corresponding digital values, and a controller having a microprocessor, a memory, and an algorithm to process the digital values relative to atrial and ventricular detection thresholds and identify therefrom atrial events and ventricular events. The identified events include stimulated and detected events and events corresponding to a same cardiac cycle. The system is preferably able to produce conventional event markers corresponding to the identified event that can be stored in memory or provided to remote programmer as known in the art. The detection circuit has a sensitivity and a corresponding detection threshold for detecting electrical activity, wherein electrical signals greater than said detection threshold correspond to an identified event. The controller algorithm performs the signal processing functions (identifying events and type of event, cardiac rates and disorders of rate and produces event markers), and includes a post ventricular atrial absolute refractory period wherein said system operates to apply said post ventricular atrial absolute refractory period in response to an identified ventricular event to inhibit the circuit from detecting electrical signals at the atrium during said period. The system also includes means for dynamically adjusting the detection threshold by a first increment for a first length of time in response to an identified ventricular event without an identified atrial event preceding said identified ventricular event in said same cardiac cycle. This adjustment may be employed by a temporary reprogramming of the detection threshold for said first duration (after which the detection threshold returns to its prior value), and may be implemented in software as storage of a reference value (i.e., a digital word) in a memory register.

The dynamically adjusting means also may temporarily increment the detection threshold by a second increment for a second length of time in response to an identified ventricular event having an identified detected atrial event preceding that ventricular event during the same cardiac cycle.

BRIEF DESCRIPTION OF THE DRAWINGS

Further benefits, features and characteristics of the present invention will become apparent to a person of ordinary skill in the art in view of the following detailed description of a preferred embodiment of the invention, made with in reference to the annexed drawings, in which:

FIG. 1 is a series of chronograms of various cardiac signals showing the consequences of the occurrence of ventricular extrasystole and the detection of far-field signals in the case of a prior art device; and FIG. 2 is a series of chronograms of various cardiac signals in accordance with a device of the present intention, illustrating the manner of preventing false diagnoses related to occurrence of ventricular extrasystoles and the detection of far-field signals.

DETAILED DESCRIPTION OF THE INVENTION

In FIGS. 1 and 2, the chronogram (a) illustrates an ECG signal on which various cardiac events follow one another. The term "events" refers to either the signals coming from a spontaneous depolarization (a detected event), or the signals resulting from stimuli applied by the apparatus (a stimulated event). These events are referred in the following way:

P or detP: spontaneous atrial cardiac event (detected)
R or detR: spontaneous ventricular cardiac event (detected)
A or StimA: stimulated atrial cardiac event (stimulated)
V or StimV: stimulated ventricular cardiac event (stimulated)

The first two cycles illustrated on each chronogram (a) correspond to spontaneous, physiological cycles, followed by a ventricular extrasystole (VES), followed by three stimulated cycles with the first cycle being an atrial and a ventricular stimulation, the second cycle being an atrial stimulation followed only by a spontaneous ventricular depolarization, and the third cycle being a spontaneous atrial depolarization followed by a ventricular stimulation.

The chronogram (b) indicates the level of the atrial detection threshold, which is fixed in the case of the prior art (FIG. 1), and which can be temporarily increased in the case of the present invention (FIG. 2).

On line (c), the post-ventricular atrial absolute refractory periods (PVAARP) are illustrated. The periods PVAARP periods are started after any ventricular event (spontaneous or stimulated) and operated to prohibit any detection of an atrial signal throughout period PVAARP. In the illustrated example, period PVAARP has a duration of 47 ms in the case of a spontaneous ventricular event (R) and 78 ms in the case of a stimulated ventricular event (V).

The line (d) illustrates a succession of the event markers assigned to the detected events as analyzed by the implantable device: atrial events P or A are above the line, and ventricular events R or V are below the line.

If one now considers the analysis of EGG of line (a) as seen by the device, i.e., as represented by the event markers of line (d), one notes that the occurrence of VES, which corresponds to a signal of a significant amplitude, induces the occurrence of a far-field phenomenon consecutive to VES. That far-field signal will be sensed by the atrial detection circuit of device and will be diagnosed as an atrial event (the first event identified as FFS on line (d)) whereas this signal is in fact only a "residue" of VES. In the same manner, a ventricular stimulation intervening with the cycle immediately following the VES also will induce a detection of a far-field signal (the second event referred to as FFS on line (d)), interpreted wrongly as an atrial event by the device. Under these conditions, for any ventricular signal a device of the prior art will see an atrial signal that can be interpreted as a P-wave, and this will distort the evaluation of the degree of association of the following ventricular event.

FIG. 2 illustrates the way in which the invention makes it possible to avoid such a false diagnosis of association, by looking to the succession of ventricular events not preceded by an associated atrial signal, revealing in particular a phenomenon of a ventricular tachycardia. To this end, the invention uses two techniques.

The first technique concerns temporarily raising the atrial detection threshold ($S_A$), by an increment $\Delta S1$ for a length of time $t_1$ in the case of a ventricular event preceded by an atrial detection in the cycle, and by a value $\Delta S_2$ for a length of time $t_2$ in the case of a ventricular event finishing a cycle without detection of a preceding atrial stimulation (i.e., a ventricular event that corresponds to the definition of a VES). This temporary increase in the threshold $S_A$ makes it possible to avoid the detection of a far-field signal consecutive to the occurrence of a VES (a signal represented, in memory, by the first event marker in dotted lines on the chronogram of line (d), just after the event marker corresponding to the VES).

The threshold values, the threshold increases and the lengths of time are advantageously independently programmable, with the threshold being programmed, for example, about 0.4 mV, and the provisional increases in threshold, for example, being established at $\Delta S_1=\Delta S_2=0.4$ mV, for lengths of time $t_1=t_2=172$ ms.

The second technique concerns, in the case of a ventricular event preceded by an atrial stimulation in the same cardiac cycle, to increase the period PVAARP by a fixed duration $\Delta t$ (for example $\Delta t=94$ ms), or to prolong this refractory period up to a predetermined duration. Either extension is sufficient to obtain the desired result. This increase in the period PVAARP operates to mask the detection of the far-field signals occurring at the time of the cycle immediately following the VES (the signal represented in memory by the second event marker in dotted lines on line (d)). The device will be able to thus detect the effective absence of atrial signals associated with several ventricular events. This will thus enable the device to quickly formulate a diagnosis of a dissociated cardiac rate if the situation continues or is repeated on the following cycles.

Suitable devices for which the present invention has application include, for example, the Defender™ and Alto™ brand of defibrillators available from Ela Médical, Montrouge France. These devices are microprocessor based systems having circuits for receiving, conditioning and processing detected electrical signals, and are capable of receiving software instructions by telemetry, storing them in memory, and then executing those instructions to perform the functions described above in implementing the present invention. The creation of suitable software instructions for controlling an implant to perform the aforementioned functions of the present invention are believed to be within the abilities of a person of ordinary skill in the art. The detection circuits used to detect the cardiac signals in the atrium and the ventricular, in the left and/or right chambers, are well known and any suitable design may be used.

One skilled in the art will appreciate that the present invention can be practiced by other than the described embodiments, which are presented for purposes of illustration and not of limitation.

We claim:

1. An active implantable medical device for monitoring cardiac activity in a patient having means for detecting ventricular events, means for detecting atrial events, means for indicating a delivery of a ventricular stimulation pulse and a delivery of an atrial stimulation pulse, means for inhibiting the atrial event detection means from detecting atrial events for a first post-ventricular atrial absolute refractory period in response to a detection of a ventricular event, the atrial event detecting means further comprising a sensitivity and a detection threshold and means for protecting against a detection of atrial signals not corresponding to an atrial event that has actually occurred;

wherein the improvement comprises:

first means for temporarily raising the detection threshold of the atrial event detecting means by a first increment for a first length of time in response to the ventricular means detecting a ventricular event without the atrial detecting means detecting a preceding atrial event during the same cycle; and second means for temporarily raising the detection threshold by a second increment for a second length of time in response to the ventricular detecting means detecting a ventricular event and the atrial detecting means detecting a preceding spontaneous atrial event during the same cycle.

2. The device of claim 1, wherein the value of each of said first and second increments is selected from between 0.2 and 0.6 mV.

3. The device of claim 2, wherein said first and second increments are of the same value.

4. The device of claim 3, wherein said first and second increments have a value of 0.4 mV.

5. The device of claim 1 wherein the value of each of said first and second lengths of time is selected from between 150 and 200 ms.

6. The device of claim 5, wherein said first and second lengths of time are of the same value.

7. The device of claim 6, wherein the value of said first and second durations is approximately 172 ms.

8. The device of claim 1, wherein the protecting means further comprises means for increasing the post-ventricular atrial absolute period refractory a predetermined duration, in response to the ventricular detecting means detecting a ventricular event and the atrial detecting means detecting a preceding stimulated atrial event during the same cycle.

9. The device of claim 8, wherein said post-ventricular atrial absolute period refractory is increased by a predetermined duration selected from between 85 and 105 ms.

10. The device of claim 9 wherein said post-ventricular atrial absolute refractory period is increased by a predetermined duration of 94 ms.

11. An apparatus for detecting cardiac activity in an active implantable medical device comprising: a system for monitoring electrical activity in an atrium and a ventricle of a patient including an atrial detection circuit to receive electrical signals from the atrium and convert the received signals to digital values, a ventricular detection circuit to receive electrical signals from a ventricle and convert the received signals to digital values, a controller having a microprocessor, a memory, and an algorithm to process the digital values and identify therefrom atrial events and ventricular events, including stimulated and detected events, and events corresponding to a same cardiac cycle; said atrial detection circuit having a sensitivity and a corresponding detection threshold wherein electrical signals greater than said detection threshold correspond to an identified atrial event; said algorithm including a post ventricular atrial absolute refractory period wherein said system operates to apply said post ventricular atrial absolute refractory period in response to an identified ventricular event to inhibit said atrial detection circuit from detecting atrium events during said period; and means for dynamically adjusting the detection threshold by a first increment for a first length of time in response to an identified ventricular event without an identified atrial event preceding said identified ventricular event in said same cardiac cycle;

wherein said dynamically adjusting means further comprises means for temporarily incrementing the detection threshold a second increment for a second length of time in response to an identified ventricular event and an identified detected atrial event preceding said ventricular event during a same cardiac cycle.

12. The device of claim 11 wherein the first and second increments each further comprise a value selected from between 0.2 and 0.6 mV.

13. The device of claim 11 wherein the first and second increments further comprise the same value.

14. The device of claim 11 wherein the first and second lengths of time are selected from between 150 and 200 ms.

15. The device of claim 14 wherein the first and second lengths of time further comprise the same value.

16. The device of claim 11 wherein the system further comprises means for increasing the post-ventricular atrial absolute refractory period by a predetermined length of time in response to an identified ventricular event and an identified stimulated atrial event preceding said ventricular event during a same cardiac cycle.

17. The device of claim 16 wherein the predetermined length of time is selected from between 85 and 105 ms.

18. The device of claim 11 wherein the system further comprises means for increasing the post-ventricular atrial absolute refractory period to a predetermined duration in response to an identified ventricular event and an identified stimulated atrial event preceding said ventricular event during a same cardiac cycle.

* * * * *